United States Patent [19] [11] 4,140,686
Kawamoto et al. [45] Feb. 20, 1979

[54] METHOD FOR PURIFYING α-AMINO-ε-CAPROLACTAM

[75] Inventors: Ichiro Kawamoto; Takeshi Sekoguchi; Yoshihiro Shibai, all of Nagoya, Japan

[73] Assignee: Toray Industries, Inc., Tokyo, Japan

[21] Appl. No.: 845,392

[22] Filed: Oct. 25, 1977

Related U.S. Application Data

[63] Continuation-in-part of Ser. No. 702,728, Jul. 6, 1976, abandoned.

[51] Int. Cl.² .................. C07D 223/10; C07D 223/12
[52] U.S. Cl. ............................................. 260/239.3 R
[58] Field of Search .................................. 260/239.3 R

[56] References Cited
U.S. PATENT DOCUMENTS 3,879,382 4/1975 Watase et al. ................ 260/239.3 R
3,898,213 8/1975 Koff ........................ 260/239.3 R Primary Examiner—Natalie Trousof
Assistant Examiner—Robert T. Bond
Attorney, Agent, or Firm—Cushman, Darby & Cushman

[57] ABSTRACT

Purified α-amino-ε-caprolactam free from not only visible ray-absorbing substances but ultra-violet ray-absorbing substances, such as, tetrahydrophenazine and octahydrophenazine, and volatile basic substances such as, ammonium salts, is obtained by dissolving a crude α-amino-ε-caprolactam in a solvent consisting of at least one alkyl ester of saturated aliphatic acid of the formula:

$$C_mH_{2m+1}COOC_nH_{2n+1}$$

wherein m is 1 or 2 and n is 1, 2, 3 or 4, at an elevated temperature at which the crude material can be completely dissolved in the solvent, cooling the solution to a lowered temperature at which the α-amino-ε-caprolactam is allowed to recrystallize from the solution, and separating the crystals of the purified α-amino-undecanoic acid from the solution.

5 Claims, No Drawings

METHOD FOR PURIFYING α-AMINO-ε-CAPROLACTAM

This application is a continuation-in-part of our application Ser. No. 702,728 filed on July 6, 1976, now abandoned.

The present invention relates to a method for purifying α-amino-ε-caprolactam. More particularly, the present invention relates to a method for purifying a crude α-amino-ε-caprolactam containing volatile basic substances, coloring substances and substances which absorb ultra-violet rays, by way of recrystallization.

It is known that α-amino-ε-caprolactam is useful as a starting material for producing lysine which is an indispensable amino acid and used as an additive to foods and feed for animals. It is obvious that in the above mentioned use lysine must be of an extremely high purity. In order to obtain the extremely high purity lysine, it is required that the starting material, α-amino-ε-caprolactam, have an extremely high purity. Accordingly, the method which is capable of producing α-amino-ε-caprolactam of an extremely high purity is very much desired for producing high purity lysine.

In general, a material, which has been produced by a chemical process, consists of a major portion consisting of an essential substance and a minor portion consisting of various sorts of other substances, namely, impurities. In the chemically produced materials, the impurities are different in chemical and physical properties from each other and form the essential substance. Accordingly, in order to separate the impurities from the essential substance, a number of different methods are available depending on the required quality of the purified essential substance and difference in chemical and physical properties of impurities from each other and from the essential substance.

In the evaluation of the quality of the chemically produced material, usually, impurities are classified depending on the chemical and physical properties thereof and it is then determined what impurities must be removed from the material in consideration of the chemical and physical properties of the impurities.

As stated above, the α-amino-ε-caprolactam is required to have a very high quality. The high quality must involve not only high colorlessness and high chemical purity but other properties. For example, the colorlessness of the α-amino-ε-caprolactam is indicated in terms of Hazen number. This Hazen number can indicate only the content of coloring substances which can absorb visible rays in the α-amino-ε-caprolactam, but can not indicate the content of colorless impurities which can not absorb visible rays. Also, the degree of purity can indicate only the content of the essential substances, but can not indicate the kind of impurities present. Accordingly, in the evaluation of the quality of the α-aminoε-caprolactam, it is important to know the kind and content of impurities, which can not be estimated from the colorlessness of the α-amino-ε-caprolactam.

The inventors have discovered that the impurities such as hydrophenazines, for example, tetrahydrophenazine and octahydrophenazine, which absorb a 290 mμ ultra-violet ray but not visible rays, and volatile basic impurities such as ammonium salts, for example, ammonium chloride and ammonium sulfate are important substances to be eliminated from the α-amino-ε-caprolactam.

As object of the present invention is to provide a method for purifying α-amino-ε-caprolactam by eliminating ultra-violet ray-absorbing impurities such as hydrophenazines, and volatile basic impurities such as ammonium salts, therefrom.

The above object can be accomplished by the method of the present invention which comprises:
dissolving a crude α-amino-ε-caprolactam containing hydrophenazines and ammonium salts into a solvent consisting of at least one alkyl ester of aliphatic carboxylic acid of the formula:

$$C_mH_{2m+1}COOC_nH_{2n+1}$$

wherein m represents an integer of 1 or 2 and n represents an integer of 1 to 4, at an elevated temperature at which said crude α-amino-ε-caprolactam is completely dissolved in said solvent;
cooling said solution prepared above to a lowered temperature at which said α-amino-ε-caprolactam is allowed to recrystallize from said solution, and;
separating the resultant crystals of said α-amino-ε-caprolactam from the solution.

The crude α-amino-ε-caprolactam can be prepared by a Beckmann rearrangement of α-amino crclohexanoneoxime hydrochloric salt in the presence of an acid catalyst.

In the method of the present invention, it is important that the specified alkyl ester of aliphatic carboxylic acid by used as a solvent for the crude α-amino-ε-caprolactam. The specified alkyl ester aliphatic carboxylic acid may be selected from the group consisting of methyl acetate, ethyl acetate, n- and iso-propyl acetates, n-, iso-, secondary- and tertiary butyl acetates, methyl propionate, ethyl propionate, n- and iso-propyl propionate and n-, iso-, secondary- and tertiary-butyl propionate. This type of the solvent is effective for holding the visible ray-absorbing substances, the ultra-violet ray-absorbing substances and the volatile basic substances in the solvent at the lowered temperature, so as to allow the α-amino-ε-caprolactam to recrystallize while leaving the above-mentioned impurities in the solution. If a solvent different from those of the present invention is used, for example, water of chloroform, the resultant crystals of the α-amino-ε-caprolactam are accompanied by both or either of the ultra-violet ray absorbing impurities and the volatile basic impurities. This fact will be illustrated by way of the comparison examples presented hereinafter.

In the method of the present invention, it is preferable that the crude α-amino-ε-caprolactam be mixed with the specified solvent, preferably, in a proportion of 1:0.5 to 3.0 by weight. The mixture is agitated and heated to an elevated temperature until the crude α-amino-ε-caprolactam is completely dissolved in the specified solvent. The elevated dissolving temperature at which the crude α-amino-ε-caprolactam can be completely dissolved in the solvent may be adjusted, preferably, in a range from 50° to 80° C., depending on the proportion of the crude α-amino-ε-caprolactam to the solvent in the mixture. If the dissolving temperature is higher than 80° C., the α-amino-ε-caprolactam might sometimes be affected by oxygen involved in the dissolving system. When the dissolving is completed, the solution is cooled to a lowered temperature while allowing the α-amino-ε-caprolactam to recrystallize from the solution. The solution is kept at the lowered temperature until the recrystallization completes. The lowered cooling temperature can be adjusted, preferably, in a range from 5° C. to 30° C., depending on the concentration of the crude α-amino-ε-caprolactam in the solvent.

In general, the lower the crystallizing temperature and the higher the concentration of the crude αamino-ε-caprolactam, the higher the viscosity of the solution. Accordingly, when the solution has a high concentration of the α-amino-ε-caprolactam and the solution is cooled to a temperature lower than 5° C., the increased viscosity of the solution might cause difficulty in the recrystallizing operation and separating operation. By the formation of crystals of the purified α-amino-ε-caprolactam, the solution is converted into the state of a slurry. The slurry is subjected to a separation of the crystals from the slurry. The separation can be effected by any of the conventional separating operations, that is, filtration or centrifugal separation, while keeping the slurry at the lowered temperature. The separated crystals may be washed with an organic solvent, preferably, the same solvet as used in the recrystallizing operation. The washed crystals are dried under a reduced pressure.

The features and advantages of the method of the invention are further illustrated by the examples set forth below, which are not intended to limit the scope of the present invention.

In the examples, the Hazen number of the purified α-amino-ε-caprolactam in the state of melt was determined by the following method.

A Standard Hazen solution was prepared by dissolving 1.246 g of potassium chloroplatinate, which contained 500 mg of platinum, and 1.00 g of cobalt chloride hexahydrate in 100 ml of hydrochloric acid. The solution was adjusted to a volume of 1000 ml by adding water thereto. The standard Hazen solution thus prepared had a Hazen number of 500. The standard Hazen solution had an absorbance of 0.674 to a visible ray having a wave length of 457 mµ, when measured using an optical glass cell having a 5 cm thickness.

Provided the melt of the α-amino-ε-caprolactam had an absorbance As, which had been measured by the same method as that for the standard Hazen solution, the Hazen number of the melt was determined in accordance with the equation:

Hazen number of melt = As × 500/0.674.

In the examples, the percent of transmission of the purified α-amino-ε-caprolactam solution was determined by the following method. 20 g of the ε-amino-ε-caprolactam was dissolved in 20 ml of water to prepare a 50% aqueous solution. The solution was subjected to measurement of the percent of transmission of an ultra-violet ray at a wave length of 290 mµ using a cell made of quarts and having a 1 cm thickness.

In the examples, the content of the volatile basic substances in the α-amino-ε-caprolactam was determined by the following method. A 50% aqueous solution was prepared by dissolving 20 g of the α-amino-ε-caprolactam in 20 ml of water and mixed with 200 ml of 1N-sodium hydroxide solution in water. The resultant aqueous solution was heated to a temperature of 98° C. for 1 hour, while allowing volatile basic substances in the solution to evaporate away from the solution. The evaporated volatile basic substances were collected and the amount thereof was determined in terms of ammonia.

EXAMPLES 1 THROUGH 4 AND COMPARISON EXAMPLES 1 AND 2

In Example 1, a four-neck flask of 500 ml having a thermometer, a stirrer and a reflax condenser, was charged with a mixture of 100 g of a crude α-amino-ε-caprolactam and 100 g of a solvent consisting of methyl acetate. The crude α-amino-ε-caprolactam was prepared by the Beckmann rearrangement of α-amino cyclohexanoneoxime hydrochloric salt in the presence of sulfuric acid catalyst at a temperature of 90° C., and contained, as impurities, octahydrophenazine, tetrahydrophenazine and ammonium sulfate. The mixture was heated to a temperature of 70° C. while stirring with the stirrer and a condensing solvent vapor was produced in the flask by means of the reflax condenser. The crude α-amino-ε-caprolactam was completely dissolved in the solvent.

The solution thus prepared was cooled to a temperature of 10° C. and kept at a temperature of 10 to 20° C. for 2 hours so as to allow the α-amino-ε-caprolactam to recrystallize from the solution. The solution was converted into a slurry. The slurry was discharged from the flask and filtered under a reduced pressure while keeping the slurry at a temperature between 10 to 20° C. The resultant crystals of purified α-amino-ε-caprolactam were separated from the filtrate. The crystals were dried at a temperature of 30° C. under a pressure of 10 mmHg.

The crystals of purified α-amino-ε-caprolactam were subjected to determination of the purity thereof by way of gas chromatography. The crystals were also subjected to measurement of the Hazen number of melt, the percent of transmission of ultra-violet rays and the content of volatile basic substances by the methods mentioned hereinbefore. The results of the measurements are indicated in the table below.

In Examples 2 through 4, procedures identical to those in Example 1 were repeated, except that ethyl acetate in Example 2, ethyl propionate in Example 3 and n-butyl acetate in Example 3 were used as the solvent in place of the methyl acetate. The results are also shown in the table below.

In Comparison Examples 1 and 2, procedures identical to those in Example 1 were repeated, except that water in Comparison Example 1 and chloroform in Comparison Example 2 were used as the solvent instead of methyl acetate. The results are also shown in the table.

|  |  | Solvent | Ratio in weight of solution to solvent | Dissolving temperature (°C.) | Recrystallizing temperature (°C.) | α-amino-ε-caprolactam Purity (%) | Hazen number of melt | Percent transmission of 290 mµ ultra-violet ray | Content of volatile basic substances (ppm) |
|---|---|---|---|---|---|---|---|---|---|
| Crude material |  | — | — | — | — | — | 610 | 0 | 286 |
| Comparative Example | 1 | Water | 1 | 70 | 10 – 20 | 99.4 | 85 | 2 | 132 |
|  | 2 | Chloroform | 1 | 70 | 10 – 20 | 99.8 | 20 | 21 | 62 |

-continued

| | | Solvent | Ratio in weight of solution to solvent | Dissolving temperature (° C.) | Recrystallizing temperature (° C.) | α-amino-ε-caprolactam | | | |
|---|---|---|---|---|---|---|---|---|---|
| | | | | | | Purity (%) | Hazen number of melt | Percent transmission of 290 mμ ultra-violet ray | Content of volatile basic substances (ppm) |
| Example | 1 | Methyl acetate | 1 | 70 | 10 – 20 | 99.9 | 20 | 97 | 3 |
| | 2 | Ethyl acetate | 1 | 70 | 10 – 20 | 99.9 | 20 | 98 | 2 |
| | 3 | Ethyl propionate | 1 | 70 | 10 – 20 | 99.9 | 20 | 97 | 3 |
| | 4 | n-Butyl acetate | 1 | 70 | 10 – 20 | 99.9 | 20 | 96 | 4 |

In view of the table, it is evident that in Comparison Example 1, wherein water was used as the solvent, the resultant purified material contained a remarkable amount of coloring substances and volatile basic substances. The purified material had an extremely poor percent of transmission of the ultra-violet ray. This means that the purified material contained a great amount of substances which absorb ultra-violet rays. Also, in Comparison Example 2, in which chloroform was used as the solvent, the resultant purified material contained a considerable amount of volatile basic substances. The purified material had a poor percent of transmission of the ultra-violet ray and, therefore, contained a considerable amount of ultra-violet ray-absorbing substances.

Composed with the above mentioned examples, the Table clearly shows that the resultant purified material in accordance with the method of the present invention has the following advantages.

1. Extremely high purity
2. Extremely small content of coloring substances
3. Extremely high percent of transmission of ultra-violet rays, namely, a small content of ultra-violet ray-absorbing substances
4. Very small content of volatile basic substances Whaat we claim is:

1. A method for purifying α-amino-ε-caprolactam comprising:
    dissolving a crude α-amino-ε-caprolactam containing hydrophenazines and ammonium salts into a solvent consisting of at least one alkyl ester of aliphatic carboxylic acid of the formula:

wherein m represents an integer of 1 to 2 and n represents an integer of 1 to 4, at an elevated temperature at which said crude α-amino-ε-caprolactam is completely dissolved in said solvent;
    cooling said solution prepared as mentioned above to a lowered temperature at which said α-amino-ε-caprolactam is allowed to recrystallize from said solution, and;
    separating the resultant crystals of said α-amino-ε-caprolactam from said solution.

2. A method as claimed in claim 1, wherein said solvent is selected from the group consisting of methyl acetate, ethyl acetate, n- and iso-propyl acetates, n-, iso-, secondary- and tertiary-butyl acetates, methyl propionate, ethyl propionate, n- and iso-propyl propionates and n-, iso-, secondary- and tertiary-butyl propionates.

3. A method as claimed in claim 1, wherein said elevated dissolving temperature is in a range from 50° C. to 80° C.

4. A method as claimed in claim 1, wherein said recrystallizing temperature is in a range from 5° C. to 30° C.

5. A method as claimed in claim 1, wherein the proportion of said crude α-amino-ε-caprolactam to said solvent is in a range from 1:0.5 to 1:3.0 by weight.

* * * * *

UNITED STATES PATENT AND TRADEMARK OFFICE
CERTIFICATE OF CORRECTION

PATENT NO. : 4,140686

DATED : February 20, 1979

INVENTOR(S) : KAWAMOTO, Ichiro; SEKOGUCHI, Takeshi & SHIBAI, Yoshihiro

It is certified that error appears in the above-identified patent and that said Letters Patent are hereby corrected as shown below:

In the cover sheet insert a line after the line (22) the following:

(30)  Foreign Application Priority Data

July 17, 1975   Japanese   50-86692

Signed and Sealed this

Eighth Day of May 1979

[SEAL]

Attest:

RUTH C. MASON
Attesting Officer

DONALD W. BANNER
Commissioner of Patents and Trademarks